US009885015B2

(12) United States Patent
Chen et al.

(10) Patent No.: US 9,885,015 B2
(45) Date of Patent: Feb. 6, 2018

(54) CHEMICAL REPROGRAMMING OF HUMAN GLIAL CELLS INTO NEURONS WITH SMALL MOLECULE COCKTAIL

(71) Applicant: The Penn State Research Foundation, University Park, PA (US)

(72) Inventors: Gong Chen, State College, PA (US); Lei Zhang, State College, PA (US); Jiuchao Yin, State College, PA (US); Ningxin Ma, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 15/367,382

(22) Filed: Dec. 2, 2016

(65) Prior Publication Data

US 2017/0159013 A1  Jun. 8, 2017

Related U.S. Application Data

(60) Provisional application No. 62/263,353, filed on Dec. 4, 2015.

(51) Int. Cl.
| | |
|---|---|
| *A61K 31/192* | (2006.01) |
| *A61K 31/175* | (2006.01) |
| *A61K 31/4418* | (2006.01) |
| *A61K 31/4545* | (2006.01) |
| *A61K 31/506* | (2006.01) |
| *A61K 33/14* | (2006.01) |
| *C12N 5/0793* | (2010.01) |
| *A61K 31/375* | (2006.01) |

(52) U.S. Cl.
CPC .......... *C12N 5/0619* (2013.01); *A61K 31/192* (2013.01); *A61K 31/375* (2013.01); *A61K 31/4418* (2013.01); *A61K 31/4545* (2013.01); *A61K 31/506* (2013.01); *A61K 33/14* (2013.01); *C12N 2506/08* (2013.01)

(58) Field of Classification Search
None
See application file for complete search history.

(56) References Cited

U.S. PATENT DOCUMENTS

2014/0024599 A1  1/2014  Chen

FOREIGN PATENT DOCUMENTS

CN  101732255 A  6/2010

OTHER PUBLICATIONS

Kim et al., J Neurochemistry, 89:324-336, 2004.*
Wang, et al., The Histone Demethylases jhdm1a/1b Enhance Somatic Cell Reprogramming in a Vitamin-C-Dependent Manner, Cell Stem Cell, vol. 9, pp. 575-587 Dec. 2, 2011.
O'Brien, et al., Validating GSK3 as an in vivo target of lithium, Biochemical Society Transactions, vol. 37, No. 5, pp. 1133-1138 Oct. 1, 2009.
Sanvitale, et al., A New Class of Small Molecule Inhibitor of BMP Signaling, PLoS One, vol. 8, No. 4, e62721, 11 pages Apr. 30, 2013.
de Sousa, et al., Lithium increases platelet serine-9 phosphorylated GSK-3β levels in drug-free bipolar disorder during depressive episodes, Journal of Psychiatric Research, vol. 62, pp. 78-83 Mar. 1, 2015.
Eriksen, et al., NSAIDs and enantiomers of flurbiprofen target γ-secretase and lower Aβ42 in vivo, American Society or Clinical Investigation, vol. 112, No. 3, pp. 440-449 Aug. 1, 2003.
Lin, et al., Effects of Pirfenidone on Proliferation, Migration, and Collagen Contraction of Human Tenon's Fibroblasts In Vitro, Investigative Ophthalmology & Visual Science, vol. 50, No. 8, pp. 3796-3770 Aug. 1, 2009.
Guo et al., In Vivo Direct Reprogramming of Reactive Glial Cells into Functional Neurons after Brain Injury and in an Alzheimer's Disease Model, Cell Stem Cell, vol. 14, Iss. 2, pp. 188-202. Feb. 6, 2014.
Zhang et al., Small Molecules Efficiently Reprogram Human Astroglial Cells into Functional Neurons, Cell Stem Cell, vol. 17, iss. 6, pp. 735-747. Dec. 3, 2015.

* cited by examiner

*Primary Examiner* — Kimberly A. Ballard
*Assistant Examiner* — Stacey MacFarlane
(74) *Attorney, Agent, or Firm* — Hodgson Russ LLP

(57) ABSTRACT

Provided are compositions, articles and methods that relate to promoting neurogenesis or neuroregeneration in mammalian nervous system. Embodiments relate to use of groups of compounds that contain Crizotinib (Cri), Flurbiprofen, Lithium Chloride (Li), Vitamin C (VC), Ceritinib (Cer) or Pirfenidone (PFD). In certain implementations glial cells are converted into functional neurons.

13 Claims, 3 Drawing Sheets
(3 of 3 Drawing Sheet(s) Filed in Color)

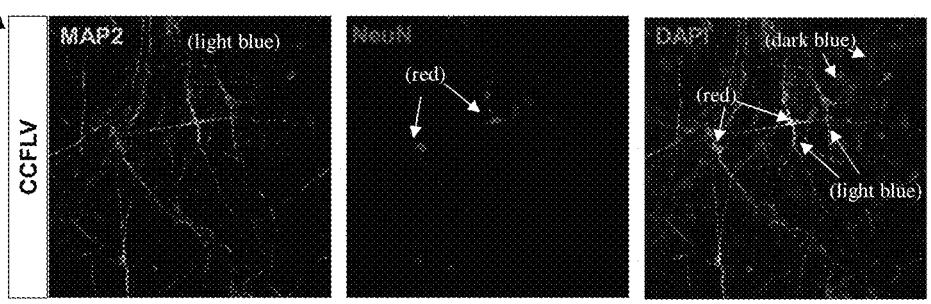
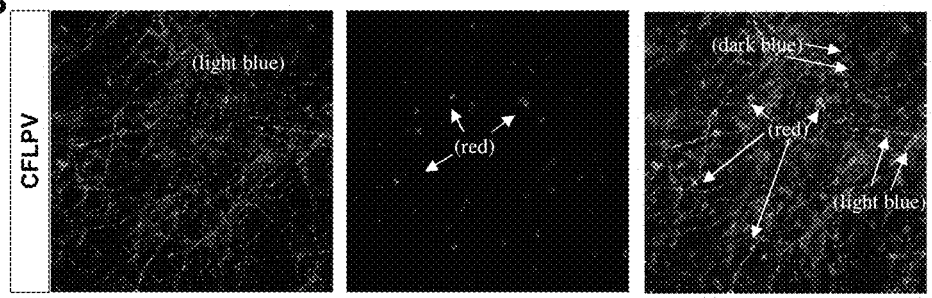

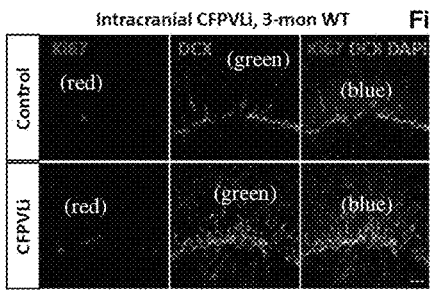
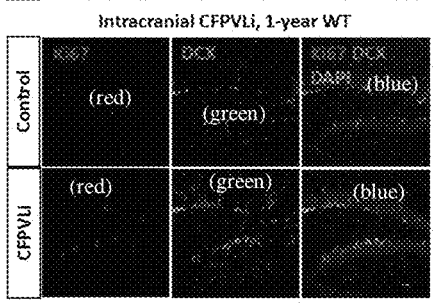
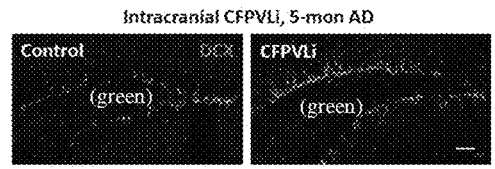
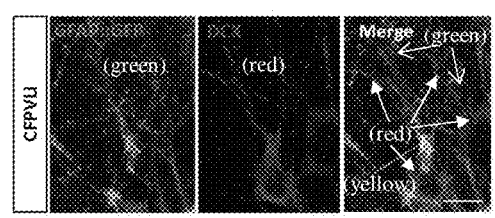
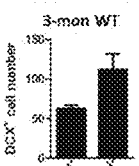
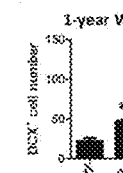
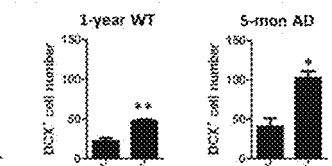
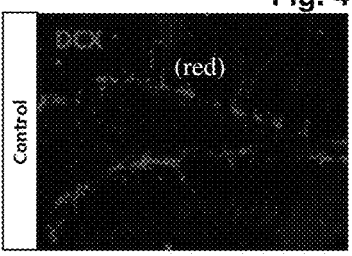
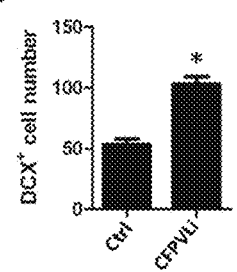

CHEMICAL REPROGRAMMING OF HUMAN GLIAL CELLS INTO NEURONS WITH SMALL MOLECULE COCKTAIL

CROSS REFERENCE TO RELATED APPLICATIONS

This application claims priority to U.S. provisional application No. 62/263,353, filed Dec. 4, 2015, the disclosure of which is incorporated herein by reference.

FIELD

The present disclosure relates generally to prophylaxis and therapy of conditions related but not limited to neural injury, neurodegeneration, aging, microcephaly, severe seizure resulting in neuronal loss, and more specifically to compositions and methods comprising combinations of chemicals for converting internal glial cells into functional neurons for neural repair, neuroregeneration, and neuroprotection.

BACKGROUND

Brain disorders such as stroke and Alzheimer's disease do not have effective therapies that can reverse their progression largely because of a lack of methods for regenerating sufficient numbers of new neurons for brain repair. The cell transplantation therapy using external cells to transplant into the brain or spinal cord (Buhnemann et al., 2006; Emborg et al., 2013; Nagai et al., 2010; Nakamura and Okano, 2013; Oki et al., 2012; Sahni and Kessler, 2010) have faced significant hurdles including immunorejection, tumorigenesis and differentiation uncertainty (Lee et al., 2013; Liu et al., 2013b; Lukovic et al., 2014). Recent studies have used viruses to express transcription factors in cells to convert them into neurons both in vitro and in vivo (Heinrich et al., 2010; Grande et al., 2013; Torper et al., 2013; Guo et al., 2014; Niu et al., 2013; Su et al., 2014). Some studies have used chemicals to convert fibroblast cells into neurons, which still need to be transplanted into the brain or spinal cord, facing all the difficulty of cell transplantation including immunorejection, tumorigenesis and differentiation uncertainty (Hu et al., 2015; Li et al., 2015). Using glial cells for neural conversion offers great advantages because they are resident cells throughout the nervous system, and are different from stem cells that are rather limited inside the nervous system. Another advantage is that glial cells can divide and regenerate themselves. Therefore, if some glial cells are converted into neurons, the remaining glial cells have the potential to divide and generate new glial cells. The present disclosure is pertinent to a need for methods for promoting conversion of glial cells into neurons.

SUMMARY

In the Figures and description of this disclosure Ceritinib is abbreviated as Cer, Pirfenidone is abbreviated as PFD, Crizotinib is abbreviated as Cri, Flurbiprofen is abbreviated as Flu, Lithium Chloride is abbreviated as Li, and Vitamin C is abbreviated as VC. In certain references to groups of compounds CC refers to Crizotinib and Certinib. F refers to Flurbiprofen. L refers to Lithium Chloride. V refers to Vitamin C. P refers to Pirfenidone. Each of these compounds is well known in the art, is commercially available, and each compound is individually approved by the U.S. Food and Drug Administration (FDA) for administration to humans for certain indications, which currently do not include any of the presently disclosed uses. The approaches embodied in this disclosure thus differ greatly from previous methods, at least in part because they involve reprogramming of glial cells using chemically synthesized compounds that are already FDA approved for use in humans. As such it does not include the risks associated with introducing exogenous genes, viral vectors, or engineered cells into patients, nor does it require manipulating stem cells or other multipotent cells in culture to differentiate them into neurons or otherwise prepare the cells for administration to a subject. Instead, the instant disclosure encompasses reprogramming glial cells already present in the individual such that they are converted into neurons using combinations of small molecules that are more fully described below. The compositions and methods are expected to provide a convenient and safe approach to treat a variety of conditions that involve neuronal deficiency, for example, neuronal loss after injury, neurodegeneration, aging, microcephaly, or severe seizure resulting in neuronal loss. It will be recognized by those skilled in the art that neural injury can result from a number of causes that are known in the art, and which typically involve astrogliosis after injury or disease processes in the central nervous system including brain and spinal cord, and peripheral nervous system. Reactive astrocytes are the main cellular component of glial scars, followed by NG2 glia and microglia. Thus, in embodiments, the present disclosure comprises converting astrocytes into neurons by chemically induced reprogramming of the astrocytes. But similar chemical reprogramming methods may also be used to convert NG2 glia or microglia or other cell types surrounding brain blood vessels into neurons.

In certain embodiments the disclosure comprises administering a combination of drugs selected from the group consisting of Ceritinib (Cer), Pirfenidone (PFD), Crizotinib (Cri), Flurbiprofen, Lithium Chloride (Li), Vitamin C (VC), and combinations thereof. Ceritinib is an anaplastic lymphoma kinase (ALK) inhibitor. Pirfenidone is a TGF-beta synthesis inhibitor. Crizotinib inhibits ALK and c-MET. Flurbiprofen is a γ-secretase inhibitor. LiCl is a Glycogen synthase kinase 3 (GSK3) inhibitor. Thus, there are a total of six agents that have been tested in furtherance of the present disclosure. In particular embodiments, the disclosure includes administering a combination of Cri/Li/Flu, plus at least one additional agent selected from PFD, Cer, VC. Groups meeting this criteria and that are demonstrated to function in the present disclosure comprise the following combinations; i) Cer/Cri/Li/Flu/VC, ii) PFD/Cri/Li/Flu/VC, iii) Cer/Cri/Li/Flu, and iv) PFD/Cri/Li/Flu. In a non-limiting demonstration the group comprises or consists of Cer/Cri/Flu/PFD/VC/Li. Any of these groups can be considered necessary and sufficient for the conversion, but the disclosure includes for each of these combinations also including at least one of the other members of the group of six agents that are not included in each group.

This disclosure includes pharmaceutical compositions comprising or consisting of any group of compounds described herein. Also provided are articles of manufacture, e.g., kits, comprising compounds and printed material. The printed material provides an indication that the compounds are for use in treating an individual in need of neurogenesis. The individual may be in need of neurogenesis for a wide variety of conditions and/or because of neuronal injury.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 1A-FIG. 11. Results showing the indicated groups of FDA-approved drugs reprogram cultured human glial cells into neurons in vitro. FIG. 1A, Combination of Crizotinib, Certinib, Flurbiprofen, Lithium Chloride, and Vitamin C converted human glial cells into neurons.

FIG. 2A-FIG. 2B. Results showing that neurons converted by the indicated compounds can survive at least 2 months in culture. Human neurons converted from astrocytes after CCFLV (FIG. 2A) or CFLPV (FIG. 2B) treatment survived at least 2 months in culture, and showed mature neuronal markers MAP2 (light blue) and NeuN (Red). DAPI (dark blue) labels cell nucleus.

FIG. 3A-FIG. 3G. Data showing intracranial injection of the indicated FDA-approved drugs increases hippocampal adult neurogenesis in the adult mouse brains. FIG. 3A shows that an intracranial injection of 2 µl small-molecule cocktail including Crizotinib 50 µM, Flurbiprofen 0.2 mM, Pirfenidone 2 µM, Vitamin C 10 mg/ml and LiCl 0.4 M into the hippocampus of 3-month-old WT mice, promoted adult neurogenesis revealed by immunostaining of newborn neuron marker doublecortin (DCX, green) and cell proliferation marker Ki67 (red). FIG. 3B. Intracranial injection of small molecule cocktail into the hippocampus of 1-year-old adult WT mice, significantly promoted adult neurogenesis in dentate gyrus (DG), supported by the increased number of DCX-positive new neurons and Ki67-positive proliferating cells. FIG. 3C. Intracranial injection of small molecule cocktail into the hippocampus of 5-month-old transgenic mouse model of Alzheimer's disease, significantly increased the number of DCX-positive new neurons in DG. FIG. 3D. In GFAP::GFP mice, astrocytes are labeled by GFP. Lineage-tracing assay indicate the DCX+ new neurons were induced from GFP-labeled astrocytes by small-molecule cocktail. FIG. 3E, FIG. 3F, and FIG. 3G present quantitative analysis showing the number of DCX+ new neurons was increased by intracranial injection of small-molecule cocktail into the hippocampus of 3-month-old WT mice (FIG. 3E), 1-year-old adult WT mice (FIG. 3F), and 5-month-old transgenic mice model of Alzheimer's disease (FIG. 3G). Student t test, *P<0.05, **P<0.01, n=3 mice per group.

FIG. 4A-FIG. 4C. Data demonstrating that intraperitoneal injection of the indicated FDA-approved drugs can also increase adult neurogenesis in the mouse brains. (FIG. 4A, FIG. 4B) Typical images showing adult neurogenesis in the hippocampal dentate gyrus after intraperitoneal injection of vehicle control (FIG. 4A, 20% Captisol), or small-molecule cocktail (FIG. 4B) including Crizotinib 50 µM, Flurbiprofen 0.2 mM, Pirfenidone 2 µM, Vitamin C 10 mg/ml and LiCl 0.4 M (3-month-old WT mice with the dose of 0.1 ml/10 g weight, injected daily for 1 month). Seven days after chemical treatment, mice were sacrificed and examined with immunostaining of newborn neuron marker DCX. (FIG. 4C) Quantitative analysis revealed an increased number of DCX+ neurons treated by the FDA-approved drug cocktail. Student's t test, *P<0.05, n=2 pairs.

DETAILED DESCRIPTION OF THE INVENTION

Figure 1A:
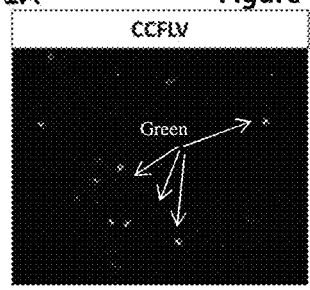

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure comprises compositions and methods that are designed to convert human glial cells into functional neurons. In embodiments the disclosure comprises but is not necessarily limited to generation of new neurons from endogenous glial cells, and can include generating new neurons from glia-like cells created due to injury or a disease condition in the central or peripheral nervous system using indicated compounds, which is expected to be useful for a variety of therapies, non-limiting embodiments of which include brain and spinal cord repair. The method generally comprises administering to an individual in need thereof an effective amount of a combination of compounds selected from the group comprising or consisting of Ceritinib (Cer), Pirfenidone (PFD), Crizotinib (Cri), Flurbiprofen (Flu), Lithium Chloride (Li), Vitamin C (VC), and combinations thereof. There are accordingly a total of six agents that have been tested as will be described more fully below. The disclosure includes administering any one or any combination of these agents. In embodiments, the combination includes two, three, four, five or all six of the compounds, and may include other compounds. In embodiments the disclosure relates to use of a combination of Cri/Li/Flu, plus at least one additional agent selected from PFD, Cer, VC.

As described in the summary above, in particular embodiments, the disclosure includes administering a group of drugs that comprise or consist of the following combinations; i) Cer/Cri/Li/Flu/VC, ii) PFD/Cri/Li/Flu/VC, iii) Cer/Cri/Li/Flu, and iv) PFD/Cri/Li/Flu. The disclosure includes for each of these combinations the option of including at least one of the other members of the group of six agents that are not included in each of the four enumerated groups. Administration of the compounds to individuals is expected to result in at least some glial cells in the individual being converted into neurons. In embodiments, alternative compounds are used, where such compounds have the same or similar effect as the compounds listed above, and wherein the administration of the combination results in conversion of glial cells into neurons. In embodiments, conversion into neurons takes place over a period of approximately 7 to 14 days.

In embodiments, the disclosure is expected to be broadly applicable for therapy of any human subject in need of neuronal generation. The need for neuronal generation arises as a consequence of any of a variety of conditions, disorders or injuries that affect neuronal function, and/or reduce the number of functional neurons in the individual. Thus, the disclosure is pertinent to prophylaxis and/or therapy of conditions which include but are not necessarily limited to ischemic brain damage, such as that caused by stroke, hypoxia or other brain trauma, or glial scarring, or neurodegeneration, or aging, or microcephaly, or severe seizure that causes neuronal loss. In embodiments the disclosure is pertinent to treating neurodegenerative disorders, including but not limited to Alzheimer's disease or other conditions which present with dementia, or Chronic Traumatic Encephalopathy (CTE) such as in athletes with a history of acute or repetitive brain trauma (i.e., concussions), or Parkinson's Disease, or Huntington's disease, or multiple sclerosis, or glioma, or spinal cord injury, or spinal muscular atrophy, or Amyotrophic lateral sclerosis (ALS). In a non-limiting embodiment a demonstration of in vivo neurogenesis promotion is demonstrated in an animal model of Alzheimer's disease.

The present disclosure does not include introduction of modified cells or viral constructs into a subject, and moreover there is no requirement for administering stem cells to an individual. For example, it is expected that aspects of the current approach will not require in vitro differentiation of cells, including stem cells, and importantly, prior art processes are distinct from our reprogramming of glial cells to neuronal cells, because stem cells can differentiate naturally into neurons but glial cells cannot become neurons unless subjected to a reprogramming process such as that demonstrated in this disclosure. Further, those skilled in the art will recognize that injecting cultured stem cells or their differentiated neurons into human subjects, and especially the brain poses significant risk to the host. Likewise, the present glia-to-neuron conversion technology is also distinct from those converting fibroblast cells into neurons in vitro, because glial cells are internal cells inside the nervous system, whereas fibroblast cells are not. Therefore, the fibroblast-converted neurons have to be transplanted into the human subject, whereas the present glia-to-neuron conversion is in situ, without any need of transplantation. In addition, as described above, it has been demonstrated that astroglial cells can be converted into neurons in vivo, but such approaches involve introduction of viral vectors, or other exogenous genes into the subjects which pose particular risks to the subject.

The present disclosure provides in various embodiments the use of completely cell and virus free pharmaceutical formulations that comprise chemical compounds that act in concert with one another to coax glial cells or glia-like cells to convert to neurons. The present disclosure provides an in vivo demonstration that these compounds can pass through the blood-brain-barrier through systemic administration and act inside the brain.

In embodiments, the disclosure comprises administering to a subject in need thereof an effective amount of one or more compositions comprising as an active ingredient a combination of compounds that are selected from Cer, PFD, Cri, Flu, Li, VC, and combinations thereof. In one aspect the disclosure includes administering a combination of Cri/Li/Flu, plus at least one additional agent selected from PFD, Cer, VC. Particular and non-limiting groups of compounds that are encompassed by the disclosure include: i) Cer/Cri/Li/Flu/VC, ii) PFD/Cri/Li/Flu/VC, iii) Cer/Cri/Li/Flu, and iv) PFD/Cri/Li/Flu. In non-limiting embodiments groups of these compounds are shown to promote neurogenesis in mouse brain using both intracranial and intraperitoneal administrations. In embodiments the group of compounds comprises or consists of Cri/Flu/PFD/VC/Li.

Each of these compounds is known in the art and is commercially available. The disclosure includes compositions and methods that comprise groups of any three, four, five, or six of these compounds, and may include additional compounds as described herein or as would otherwise be apparent to one skilled in the art, given the benefit of the present disclosure. The disclosure includes pharmaceutically acceptable salts of these compounds, analogs of the compounds and salts, and compounds which exert the same or similar functions as the compounds, provided that administration of a combination of them to an individual results in conversion of glial cells to neurons. In general reference to any particular compound described herein for use of conversion of glial cells to neurons includes pharmaceutically acceptable salts of the compounds.

In an embodiment, the disclosure includes administering to an individual a combination of compounds (concurrently or sequentially), wherein the combination comprises or consists of Cri/Li/Flu, plus at least one, or only one, additional agent selected from PFD, Cer, VC.

It will be apparent from the description, examples and figures of this disclosure that we have discovered that in combination the small molecules as described herein are capable of directly reprogramming human astrocytes into functional neurons. Because these chemicals are approved by FDA for the treatment of humans or can be obtained over the counter in drug stores, they are relatively safe and are expected to result in a convenient approach to chemical delivery for therapy of a wide variety of neural injuries and neurodegenerative conditions, including but not necessarily limited to stroke and Alzheimer's disease.

In general, methods of the disclosure comprise administering an effective amount of the compounds described herein to a subject such that the number of neurons in the individual is increased. The compounds can be administered in amounts that are the same or similar to those for which FDA approval is already in place. Dosages for each of the FDA approved drugs can be found, for example, in www.accessdata.fda.gov/scripts/cder/drugsatfda/. In embodiments, glial cells, such as astrocytes in the individual are reprogrammed so that they are converted into neurons. In embodiments, the newly generated neurons comprise glutamatergic neurons. In embodiments, the disclosure is expected to facilitate development of new cortical forebrain neurons, or midbrain neurons, or hindbrain neurons, or spinal cord neurons, or peripheral neurons, or combinations thereof by using methods described herein adapted as necessary by those skilled in the art in a manner that will be apparent given the benefit of the present disclosure. In embodiments, reprogrammed neurons are characterized by expression of neuronal markers that include but are not necessarily limited to Dcx and NeuN. In embodiments, cells in the brain, such as glial cells, are converted to neurons. In embodiments, the neurons are functional neurons. Functional neurons can exhibit properties which can comprise but are not necessarily limited to firing repetitive action potentials, developing a plurality of dendritic branches, and release of neurotransmitters, including but not necessarily limited to Glutamate (glutamic acid), dopamine, acetylcholine, serotonin, Norepinephrine (noradrenaline), and γ-Aminobutyric acid (GABA).

Data presented in this disclosure demonstrate at least the following: Groups of compounds that comprise Cri/Li/Flu and at least one of Cer, VC or PFD are effective in generating human neurons from human glial cells in vitro. In particular, each of the groups i) Cer/Cri/Li/Flu/VC, ii) PFD/Cri/Li/Flu/VC, iii) Cer/Cri/Li/Flu and iv) PFD/Cri/Li/Flu not only converted human astrocytes into neurons (FIGS. 1A-1F), the converted neurons were able to survive in culture for at least two months (FIGS. 2A and 2B). FIG.

Figure 1B:
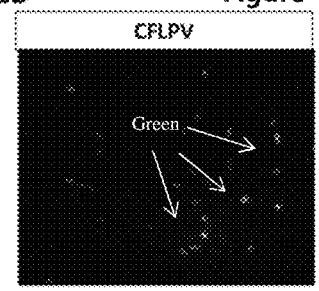
FIG. 1B, Combination of Crizotinib, Flurbiprofen, Lithium Chloride, Pirfenidone, and Vitamin C converted human glial cells into neurons.
Figure 1C:
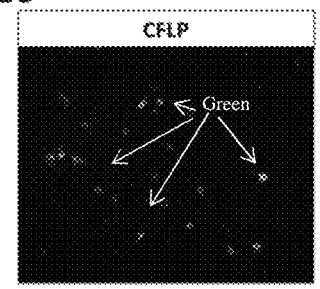
FIG. 1C, combination of Crizotinib, Flurbiprofen, Lithium Chloride, and Pirfenidone converted human glial cells into neurons.
Figure 1D:
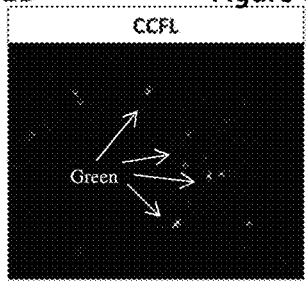
FIG. 1D, combination of Crizotinib, Certinib, Flurbiprofen, and Lithium Chloride, converted human glial cells into neurons.
Figure 1E:
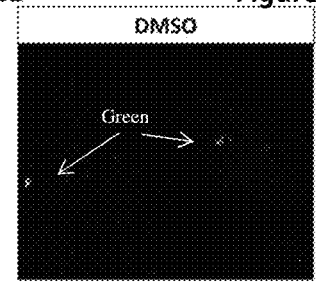
FIG. 1E, vehicle control 0.2% DMSO, the solvent for Cer, PFD, Cri and Flu, showed very few NeuN+ cells after 14 days.
Figure 1F:
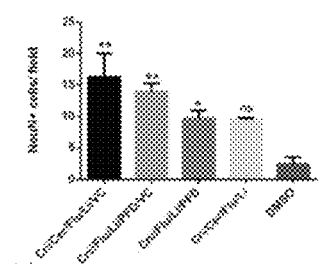
FIG. 1F, Quantitative analyses showing significant increase of NeuN+ cell numbers after drug-treatment.
Figure 1G:
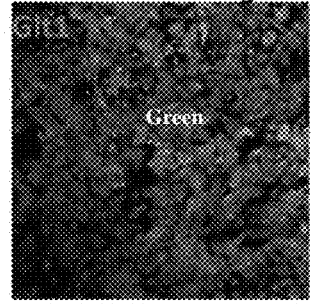
FIG. 1G. Characterization of human astrocytes with the immunostaining of astrocyte-specific marker glutamate transporter 1 (Glt1) (Green, FIG. 1G), and human nuclei marker HuNu (Blue, FIG. 1H), and the overlay image (FIG. 1I).
Figure 1H:
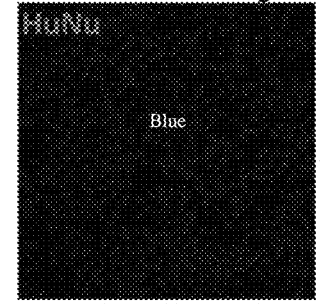
Figure 1I:
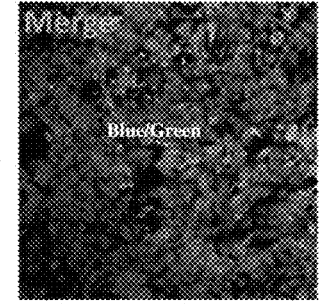

1G provides a characterization of human astrocytes with the immunostaining of the astrocyte-specific marker glutamate transporter 1 (Glt1) (Green, FIG. 1G), and human nuclei marker HuNu (Blue, FIG. 1H), and the overlay image (FIG. 1I).

Furthermore, the disclosure provides non-limiting demonstrations of such an approach in vivo. In particular, both intracranial (FIG. 3) and intraperitoneal administration (FIG. 4) results in an increase in neurogenesis in mammalian brain. The disclosure demonstrates achieving this not only in adult mouse brain, but also in the brain of a mouse that has been engineered to model Alzheimer's disease (e.g., FIG. 3C). Thus, the disclosure provides working examples of promoting in vivo neurogenesis in mammalian brain. Moreover, and without intending to be bound by any particular theory, it is believed that the disclosure proves that there is sufficient crossing of the blood-brain barrier (e.g., the i.p. administration of FIG. 4) such that the present disclosure is suitable for a variety of routes of administration. In certain and non-limiting embodiments, in vivo neurogenesis using an administration that is not limited to intracranial administration is promoted using the group of compounds comprising or consisting of Cri/Flu/PFD/VC/Li. But based on the data of this disclosure taken as a whole, it is expected that groups of compounds that comprise at least three of Cri/Li/Flu/Cer/VC/PFD will also promote neurogenesis without being limited to intracranial administration. In embodiments, Cri/Li/Flu and at least one of Cer, VC or PFD will also promote neurogenesis in mammalian brain without being limited to intracranial administration. Also without being constrained by any particular theory, it is considered that mouse data presented herein, particularly when viewed in combination with the results obtained with human cells, provides a basis for predicting that in vivo administration of groups of compounds of this disclosure to humans will be effective in promoting neurogenesis in human brain.

Compositions comprising the compounds of this disclosure can be provided in pharmaceutical formulations. The form of pharmaceutical preparation is not particularly limited, but generally comprises these active ingredients and at least one inactive ingredient. In certain embodiments suitable pharmaceutical compositions can be prepared by mixing any one or combination of the compounds with a pharmaceutically-acceptable carrier, diluent or excipient, and suitable such components are well known in the art. Some examples of such carriers, diluents and excipients can be found in: Remington: The Science and Practice of Pharmacy (2005) 21st Edition, Philadelphia, Pa. Lippincott Williams & Wilkins. In embodiments, the pharmaceutical formulations are suitable for delivering the active ingredients across the blood-brain barrier, and/or to the spinal cord or other components of the central nervous system. Such compositions can comprise, for example, lipid formulations or other nano-particle based delivery systems.

In one embodiment the pharmaceutical formulation is suitable for oral administration, and thus can be provided in an aerosolized, liquid or solid dosage form. Solid dosage forms include but are not necessarily limited to tablets, capsules, caplets, and strips, for swallowing or oral dissolution, and may be provided for rapid or extended release, or to release distinct compounds in a desirable series over a period of time. Separate pharmaceutical compositions comprising one or any combination of the compounds can also be used. Thus the pharmaceutical formulations can comprise Cri/Li/Flu, plus at least one additional agent selected from PFD, Cer, VC. It should be understood that any of the compounds described herein can be excluded from the compositions and methods of the invention.

With respect to the administration of the pharmaceutical formulations, the route of administration can be any suitable route. In embodiments, the composition comprising the compound(s) is delivered orally. In other non-limiting embodiments, the composition is administered intravenously, parenterally, subcutaneously, intraperitoneally, transdermally, by intranasal instillation, by implantation, or intraarterially. In embodiments, an implantable medical device can be used, such as a pump, including but not limited to an osmotic pump. In embodiments the compositions comprising the compounds is delivered via an intracranial route.

Appropriate dosing of the compound(s) can be determined in conjunction with the knowledge of the skilled artisan, given the benefit of the present disclosure. In embodiments, the weight and age of the individual, personal history of neuronal damage or disease and risk for experiencing same neuronal damage, or the presence of glial scarring or reactive gliosis, may be taken into account when determining an effective amount of the active ingredient and dosing regimen. In embodiments the compounds are administered in an amount of about 0.01 nmol to about 500 nmol a day, inclusive, and including all integers and ranges therebetween, depending on which delivering method being used. In embodiments, the compounds are provided in a single, multiple, or controlled release dose regimen.

In certain embodiments Ceritinib is used in a concentration of about 50 nM, which may be adjusted when administered to human patients to achieve a concentration in human blood of approximately 5-500 nM. For pirfenidone, a suitable concentration may be approximately 5 nM. For crizotinib, suitable concentration may be approximately 125 nM. For Flurbiprofen, suitable concentration may be approximately 500 nM. For LiCl a suitable concentration may be approximately 2 mM. For Vitamin C, suitable concentration may be approximately 50 ug/mL.

In certain embodiments the disclosure includes nutraceutical compositions, which are designed to impart to an individual a beneficial effect that is related to improved neuronal health and/or function. In certain embodiments, the compositions of the invention can be used to improve the general well-being of an individual, or the cognitive capability of an individual, such as for improved memory or maintenance of memory. In embodiments the compositions are useful for improving any or all of short term memory, long term memory, or motor skills, including but not necessarily limited to gross and fine motor skills. Thus, use of nutritional supplements comprising the small molecules described herein are encompassed by this disclosure.

In one embodiment, the disclosure includes an article of manufacture. In certain aspects, the article of manufacture includes a closed or sealed package that contains one or a combination of the compounds described herein, such as in separate tablets, capsules or the like. The package can comprise one or more containers, such as closed or sealed vials, bottles, blister (bubble) packs, or any other suitable packaging for the sale, or distribution, or use of pharmaceutical agents. Thus, the package can contain pharmaceutical compositions which Cri/Li/Flu, plus at least one additional agent selected from PFD, Cer, VC, and/or other compounds that are described herein and as otherwise be recognized as suitable additions by those skilled in the art. Any one or all of these compounds can be included, and each can be provided separately or in combination with one or more of the others in the same or distinct dosage formulations so that they can be delivered concurrently, or sequentially.

In addition to the pharmaceutical compositions, the package may contain printed information. The printed information can be provided on a label, or on a paper insert, or printed on the packaging material itself. The printed information can include information that identifies the active agents in the package, the amounts and types of inactive ingredients, an indication of what condition(s) the pharmaceutical composition(s) is intended to treat, and instructions for taking the pharmaceutical composition, such as the number of doses to take over a given period of time, the order to take the compositions, and the like. Thus, in various embodiments the disclosure includes a pharmaceutical composition of the invention packaged in a packaging material and identified in print, on or in the packaging material, that the composition is for use in the treatment or prophylaxis of any disease, condition or disorder that is related to a deterioration of neurons, an insufficiency of neurons, or a defect in the function of neurons. In another embodiment, instead of a pharmaceutical composition, the disclosure includes a nutraceutical formulation(s), and the printed material provides information about use of such a formulation(s) for improving cognitive function, memory, motor function, overall well-being, or the like.

The following specific examples are provided to illustrate the invention, but are not intended to be limiting in any way.

EXAMPLE 1

This Example demonstrates that groups of the FDA-approved drugs discussed herein can convert human glial cells into neurons in vitro.

The results were obtained by treatment of human astrocytes (HA1800, ScienCell Inc.) with a combination of Certinib (50 nM, Cer), Crizotinib (125 nM, Cri), Lithium Chloride (2 mM, Li), Flurbiprofen (500 nM, Flu), Pirfenidone (PFD, 5 nM), and Vitamin C (50 ug/mL, VC) together, or in different combinations as indicated for six days, which converted human astrocytes into neurons. Medium with drugs were changed every two days. 14 days after drug addition, cells were immunostained for neuronal marker NeuN. The micrograph shows many human glial cells converted into neurons. FIG. 1A, Combination of Crizotinib, Certinib, Flurbiprofen, Lithium Chloride, and Vitamin C converted human glial cells into neurons. FIG. 1B, Combination of Crizotinib, Flurbiprofen, Lithium Chloride, Pirfenidone, and Vitamin C converted human glial cells into neurons. FIG. 1C, combination of Crizotinib, Flurbiprofen, Lithium Chloride, and Pirfenidone converted human glial cells into neurons. FIG. 1D, combination of Crizotinib, Certinib, Flurbiprofen, and Lithium Chloride, converted human glial cells into neurons. FIG. 1E, vehicle control 0.2% DMSO, the solvent for Cer, PFD, Cri and Flu, showed very few NeuN+ cells after 14 days. FIG. 1F, Quantitative analyses showing significant increase of NeuN+ cell numbers after drug-treatment: CCFLV (56.0±12.9 NeuN+ cells per field, 20× lens, 0.1 mm2), CFLPV (47.8±4.7, NeuN+ cells per field), CFLP (33.3±4.3 NeuN+ cells per field), CCFL (32.4±1.3 NeuN+ cells per field), compared to DMSO control group (6.6±2.7 NeuN+ cells per field). ***P<0.001, *P<0.05, One-Way ANOVA followed with Dunnett's multiple comparisons test.

FIGS. 2A-FIG. 2B provide results showing that neurons converted by the indicated compounds can survive at least 2 months in culture. In particular, human neurons converted from astrocytes after CCFLV (FIG. 2A) or CFLPV (FIG. 2B) treatment survived at least 2 months in culture, and showed mature neuronal markers MAP2 (light blue) and NeuN (Red). DAPI (dark blue) labels cell nucleus.

EXAMPLE 2

This Example provides a non-limiting example of an in vivo implementation of an aspect of this disclosure using intracranial administration of groups of compounds in adult mice, as well as in a transgenic mouse model of Alzheimer's disease. In particular, FIG. 3A shows that an intracranial injection of 2 µl small-molecule cocktail including Crizotinib 50 µM, Flurbiprofen 0.2 mM, Pirfenidone 2 µM, Vitamin C 10 mg/ml and LiCl 0.4 M into the hippocampus of 3-month-old WT mice, promoted adult neurogenesis revealed by immunostaining of newborn neuron marker doublecortin (DCX, green) and cell proliferation marker Ki67 (red). FIG. 3B. Intracranial injection of small molecule cocktail into the hippocampus of 1-year-old adult WT mice, significantly promoted adult neurogenesis in dentate gyrus (DG), supported by the increased number of DCX-positive new neurons and Ki67-positive proliferating cells. FIG. 3C. Intracranial injection of small molecule cocktail into the hippocampus of 5-month-old transgenic mouse model of Alzheimer's disease, significantly increased the number of DCX-positive new neurons in DG. FIG. 3D. In GFAP::GFP mice, astrocytes are labeled by GFP. Lineage-tracing assay indicate the DCX+ new neurons were induced from GFP-labeled astrocytes by small-molecule cocktail. FIG. 3E, FIG. 3F, and FIG. 3G present quantitative analysis showing the number of DCX+ new neurons was increased by intracranial injection of small-molecule cocktail into the hippocampus of 3-month-old WT mice (FIG. 3E), 1-year-old adult WT mice (FIG. 3F), and 5-month-old transgenic mice model of Alzheimer's disease (FIG. 3G). Student t test, *P<0.05, **P<0.01, n=3 mice per group.

EXAMPLE 3

This Example provides a demonstration that intraperitoneal injection of a group of the FDA-approved drugs described herein can also increase adult neurogenesis in mouse brain. In particular, FIG. 4A and FIG. 4B provide representative images showing adult neurogenesis in the hippocampal dentate gyrus after intraperitoneal injection of vehicle control (FIG. 4A, 20% Captisol), or compound group cocktail (FIG. 4B) including Crizotinib 50 µM, Flurbiprofen 0.2 mM, Pirfenidone 2 µM, Vitamin C 10 mg/ml and LiCl 0.4 M (3-month-old WT mice with the dose of 0.1 ml/10 g weight, injected daily for 1 month). Seven days after chemical treatment, mice were sacrificed and examined with immunostaining of newborn neuron marker DCX. (FIG. 4C) Quantitative analysis revealed an increased number of DCX+ neurons treated by the FDA-approved drug cocktail. Student's t test, *P<0.05, n=2 pairs.

While the invention has been described through specific embodiments, routine modifications will be apparent to those skilled in the art and such modifications are intended to be within the scope of the present invention.

What is claimed is:

1. A method for generating neurons comprising contacting glial cells with a group of compounds comprising a combination of at least four of Crizotinib (Cri), Flurbiprofen (Flu), Lithium Chloride (Li), Vitamin C (VC), Ceritinib (Cer) and Pirfenidone (PFD).

2. The method of claim 1, wherein the group comprises at least the Cri, Flu, VC and PFD.

3. The method of claim 1, wherein the group comprises five of the compounds.

4. The method of claim 1 wherein the group consists of four of the compounds.

5. The method of claim 1, wherein the group consists of five of the compounds.

6. The method of claim 1, wherein the group comprises: the Cri, Flu, VC, PFD and Li.

7. The method of claim 1, wherein the group does not comprise the Li.

8. The method of claim 1, wherein the group comprises at least the Cri, Flu, VC and PFD, and wherein the group does not comprise the Li.

9. The method of claim 1 wherein the glial cells are in brain, or spinal cord, or peripheral nervous system, of a mammal.

10. The method of claim 9, wherein the group comprises the Cri, Flu, VC, PFD and Li.

11. The method of claim 9, wherein the group is administered to an individual in need of the neurons due to a condition that comprises neuronal loss and/or glial scarring and/or neural injury, and/or aging, or neurodegeneration, or microcephaly, or severe seizure.

12. The method of claim 9, wherein the individual is in need of the neurons due to ischemic brain damage.

13. The method of claim 9, wherein the individual has been diagnosed with or is suspected of having Alzheimer's disease.

* * * * *